United States Patent [19]
Schaefer et al.

[11] Patent Number: 5,203,330
[45] Date of Patent: Apr. 20, 1993

[54] DISPOSABLE ELECTRODES FOR ELECTROMYOGRAPHY (EMG) AND NERVE CONDUCTION VELOCITY (NCV) AND KIT CONTAINING SAME

[75] Inventors: Alan J. Schaefer, Spring Valley; Arthur Blumenfeld, Brewster, both of N.Y.; Finn Pedersen, Stenlose; Carsten Stabell, Bronshoj, both of Denmark

[73] Assignee: Vickers PLC, London, England

[21] Appl. No.: 661,476

[22] Filed: Feb. 26, 1991

[51] Int. Cl.[5] .................... A61B 5/04; A61B 5/0492
[52] U.S. Cl. .................... 128/640; 128/798; 128/802
[58] Field of Search .................... 128/639–641, 128/798, 802, 803

[56] References Cited

U.S. PATENT DOCUMENTS

| | | | |
|---|---|---|---|
| 4,640,289 | 2/1987 | Craighead | 128/639 |
| 4,798,208 | 1/1989 | Faasse, Jr. | 128/640 |
| 4,838,273 | 6/1989 | Cartmell | 128/640 |
| 4,848,353 | 7/1989 | Engel | 128/640 |
| 4,911,657 | 3/1990 | Berlin | 128/640 X |
| 4,934,383 | 6/1990 | Glumac | 128/798 |

Primary Examiner—Lee S. Cohen
Attorney, Agent, or Firm—Charles E. Baxley

[57] ABSTRACT

A disposable electrode for use in electromyography and/or nerve conduction velocity testing has a tab for connection to a cable connector and is laminated of a plurality of layers including first and second outer layers. The first layer is a backing member with exposed adhesive, a hydrogel layer intermediate the outer layers and a conductive foil layer between the hydrogel layer and the second outer layer. The electrode may be a disc electrode, a ground electrode or an elongated flexible digital ring electrode. The disc electrode includes two identical disc electrode elements having circular portions separably joined to each other at a central portion and the tab of each element is remote from the central portion. A kit contains a plurality of disposable electrodes packaged in a blister pack, the packaged electrodes including a plurality of such disc electrodes, a plurality of such ground electrodes and a plurality of such elongated flexible digital ring electrodes.

8 Claims, 3 Drawing Sheets

DISPOSABLE ELECTRODES FOR ELECTROMYOGRAPHY (EMG) AND NERVE CONDUCTION VELOCITY (NCV) AND KIT CONTAINING SAME

BACKGROUND OF THE INVENTION

This invention relates to electrodes, particularly for use in Electromyography (EMG) and Nerve Conduction Velocity (NCV) measurement, and more particularly to such electrodes that are disposable. The invention further relates to a kit containing such electrodes.

The invention presents a disposable disc electrode, a disposable ground electrode and a disposable digital ring electrode and a kit containing same.

EMG is the study of electrical activity of nerves and muscles. It is useful in diagnosis of diseases such as Carpal Tunnel, Amyotrophic Lateral Sclerosis (ALS), Polio and Myasthenia Gravis.

The examination has two portions which vary significantly in practice and procedure:

1. Needle EMG: This portion of the examination is a volitional recording made from within the muscle, utilizing a needle electrode—sometimes with a surface reference electrode—and requiring a grounding electrode for grounding the patient.

The frequency of response is typically 2 Hz to 10 khz with amplitudes varying from 20 Uv to as much as 10 mV. Electrodes are moved several times within an examination procedure. Impedance of the electrode/patient interface is typically 15-20 k ohm or more. It is not typically measured nor is any pre-application prepping done to the skin.

2. NCV: This portion of the examination is an evoked response using an electrical stimulus applied superficially to a nerve. The electrodes used for stimulating and recording are often used interchangeably. The sensory NCV involves stimulating and recording from nerves. A typical stimulus of 0.1 ms-50-75 volts—25 Ma is given superficially.

The response occurs 1.5 to 4 ms after the stimulus. Characteristics are 20 Hz-2 khz, with amplitude 10 Uv to 50 Uv, typically. One set of electrodes is usually placed around a digit—either fingers or toes. This electrode is typically designed as a wraparound. The other set of electrodes is placed on a flatter portion of the body—usually at the wrist, or on the foot—and is usually a set of 10 mm discs.

The Motor Nerve Conduction involves stimulating a nerve superficially and recording superficially from a muscle. The stimulus is typically 150 V 0.1 ms—duration 60 Ma, applied through handheld or taped on electrodes about 10 mm diameter with spacing of 1-2 inches between; 3 or 4 different stimulating sites are used for each muscle. The response follows the stimulus by 2-15 ms, having an amplitude of 1 mV-50 mV and bandpass of 2 Hz-10 kHz.

The EMG/NCV examination requires use of a variety of surface electrodes for recording and stimulation. Current technology utilizes reusable, stainless steel or dampened felt electrodes in varying shapes and sizes. The electrodes are fastened in place with adhesive tape or VELCRO hook and loop connected straps after either wetting or applying electrolyte.

Some technicians use mild abrasives to lower skin resistance prior to electrode application. During the test procedure gel, tape, etc., are used each time electrodes are moved, which is typically 12 times during an examination. After testing is completed, the electrodes must be washed and, ideally, disinfected. However, with the advent of disposable EMG needles already accepted in the laboratory, there is a growing preference for the remainder of the examination electrodes to be disposable.

The primary advantages of the electrodes according to the present invention are as follows:

a. No need for additional paste, tape.
b. Better recording using silver chloride.
c. Faster application.
d. No electrode cleanup.
e. Faster patient cleanup.
f. Reduced risk of contamination.
g. Cost recoverable and controlled.
h. Ability to be moved 4 or 5 times before adhesive failure.

Currently, make-do electrodes (disposable EMG or TENS) are being furnished for EMG/NCV use, but none cover the complete functional EMD/NCV requirements. This invention presents a kit containing the three different types of electrodes typically used in the EMG/NCV examinations. Disposability of the inventive electrodes means that physicians and technicians are enabled to enjoy the convenience of not cleaning electrodes and not having to deal with the patient preparation process. Accordingly, important objects of the invention are to provide disposable electrodes that attain the aforementioned advantages.

A patentability search on this disclosure found the following United States Patents:

| U.S. Pat. No. | Date | Inventor(s) |
| --- | --- | --- |
| 4,409,981 | October 18, 1983 | Lundberg |
| 4,524,087 | June 18, 1985 | Engel |
| 4,635,642 | January 13, 1987 | Cartwell et al. |
| 4,640,289 | February 3, 1987 | Craighead |
| 4,699,679 | October 13, 1987 | Cartwell et al. |
| 4,732,111 | January 26, 1988 | Muttitt |
| 4,742,828 | May 10, 1988 | Lundstrom |
| 4,768,514 | September 6, 1988 | De Marzo |
| 4,852,571 | August 1, 1989 | Gadsby et al. |
| 4,890,622 | January 2, 1990 | Ferrari |

Of the foregoing patents, it is believed that those to Lundberg, Engel and Gadsby et al., come closer than any of the others to being pertinent to the present invention.

SUMMARY OF THE INVENTION

This invention presents a disposable electrode for use in electromyography (EMG) and/or nerve conduction velocity (NCV) testing. The electrode has a tab for connection to a cable connector and is laminated of a plurality of layers including first and second outer layers. The first outer layer is a backing member with exposable adhesive thereon, a hydrogel layer intermediate the outer layers and a conductive foil layer between the hydrogel layer and the second outer layer.

The electrode is one of three types, a disc electrode, a ground electrode and an elongated flexible digital ring electrode.

The disc electrode comprises two identical disc electrode elements having circular portions separably joined to each other at a central portion whereby the electrode elements can be used together in a paired mode or separately in a detached mode. The tab of each element is remote from the central configuration.

The disc electrode has two circular conductive gel areas, each 10 mm in diameter. The rest of the contact surface is nonconductive. The other electrodes are conductive over their entire contact surfaces.

A kit contains a plurality of such disposable EMG and/or NCV electrodes packaged in a blister pack.

DESCRIPTION OF THE INVENTION

Figure 1:
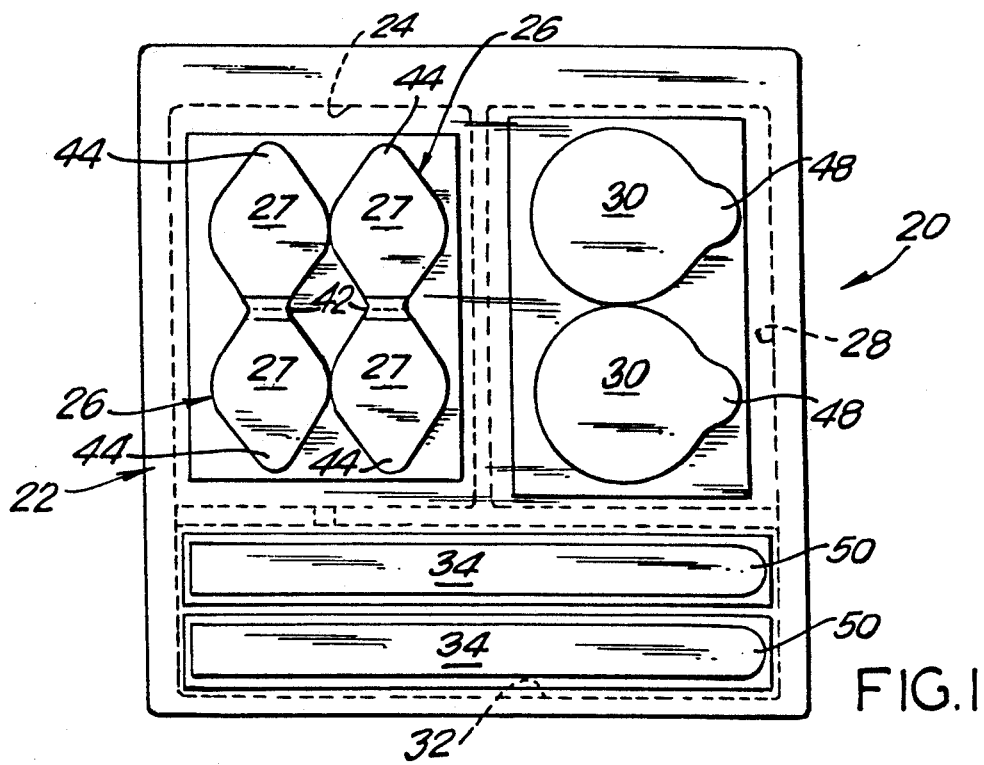
FIG. 1 is a plan view of a kit containing a plurality of each of first, second and third types of electrodes according to this invention packaged in a blister pack.

FIG. 1 shows in plan a kit 20 embodying the invention. Kit 20 contains two of each of first, second and third types of disposable inventive electrodes packaged in a blister pack 22. Blister pack 22 has a cavity 24 containing two of the first type of electrodes, these being disc electrodes 26, a cavity 28 containing two of the second type of electrodes, these being ground electrodes 30, and a cavity 32 containing two of the third type of electrodes, these being digital ring electrodes 34. Contents of blister pack 22, i.e., disc electrodes 26, ground electrodes 30 and digital ring electrodes 34, are what will typically be used in an EMG/NCV examination.

Figure 2:
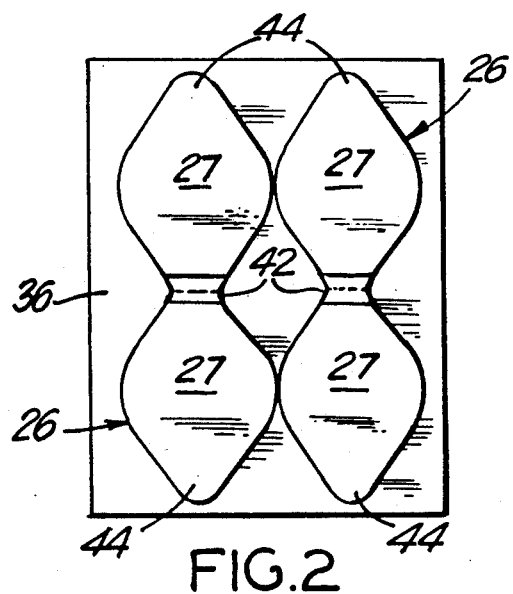
FIG. 2, 3 and 4 are enlarged plan views of each of the three types of inventive electrodes packaged in the kit of FIG. 1.
Figure 3:
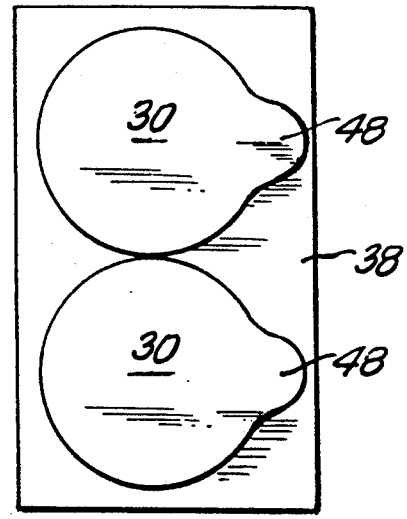
Figure 4:
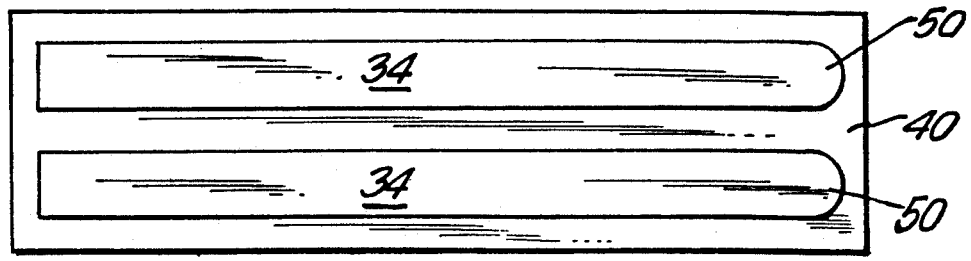

As is seen more clearly in FIGS. 2, 3 and 4, each of o electrodes 26, 30 and 34 includes, in the packaged condition, a backing layer or member to protect the electrodes until use. Electrodes 26 are shown on a backing member 36, electrodes 30 on a backing member 38 and electrodes 34 on a backing member 40.

Figure 5:
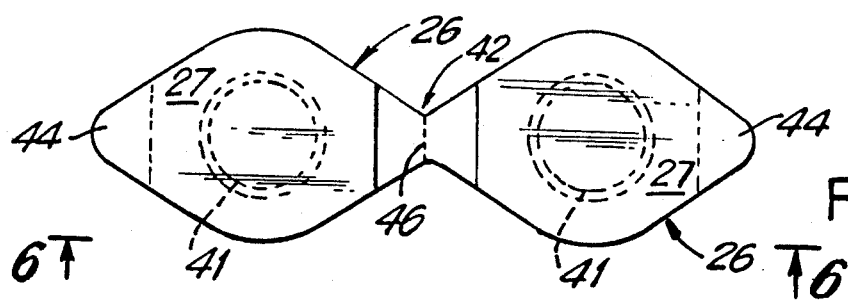
FIG. 5 is a further enlarged plan view of the first type of inventive electrode, this being a disc electrode.

Each disc electrode 26 is a double electrode, comprising two identical electrode elements 27 in one, preferably with two circular conductive gel areas 41 each 10 mm in diameter. The rest of the outer surface is nonconductive. Each electrode element 27 is joined to its neighbor at a central portion 42 that spaces each electrode element 27 a controlled constant distance from its attached neighbor. The end of each electrode element 27 remote from portion 42 has an arcuate tab 44 for connection to a cable connector (not shown). Between central portion 42 and tab 44 each of the two electrode elements 27 is disc-shaped. Electrode elements 27 can be used in a paired mode or separated, if desired, along a perforation 46 at the central portion 42 to permit the separated electrode elements 27 to be used in a detached mode at different locations or at different times, thus giving each double disc electrode 26 great versatility in use. As shown in FIGS. 1, 2 and 5, central portion 42 is of wasp-waist configuration, but this configuration is by way of example only and is by no means necessary. In this connection, see FIG. 11 and the description thereof.

Figure 6:
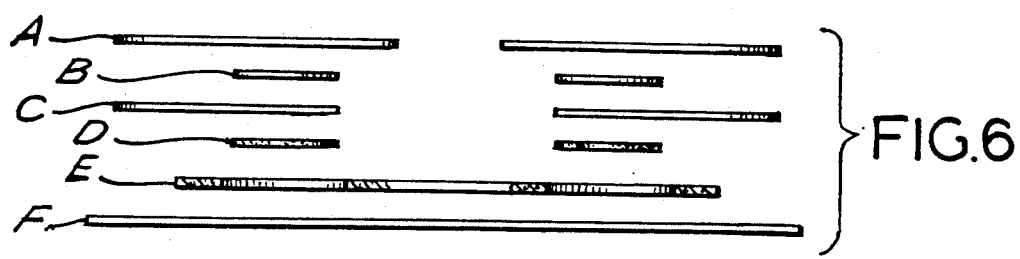
FIG. 6 is a side view of the electrode of FIG. 5 showing the laminations thereof separated, substantially on line 6—6 of FIG. 5.
Figure 7:
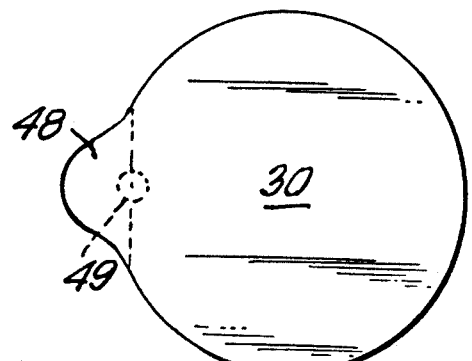
FIG. 7 is a further enlarged plan view of the second type of inventive electrode, this being a ground electrode.

Disc electrode 26 is made up of a plurality of laminations or layers that are shown separated in FIG. 6. To proceed inwardly toward the patient's skin from the outer face of disc electrode 26, layer A is a label, layer B is foam, layer C is conductive foil having a coating of silver/silver chloride, layer D is hydrogel/conductive adhesive, layer E is foam and layer F is a backing sheet, which is really the same as backing member 36.

Figure 8:
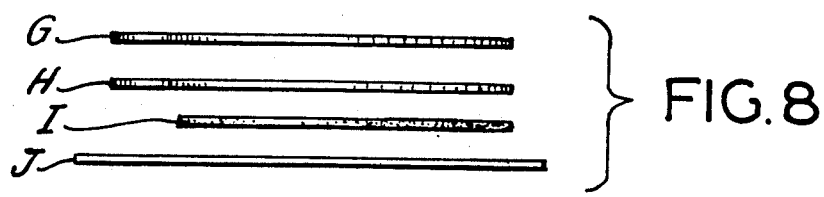
FIG. 8 is a side view of the electrode of FIG. 7 showing the laminations thereof separated, substantially on line 8—8 of FIG. 7.
Figure 9:
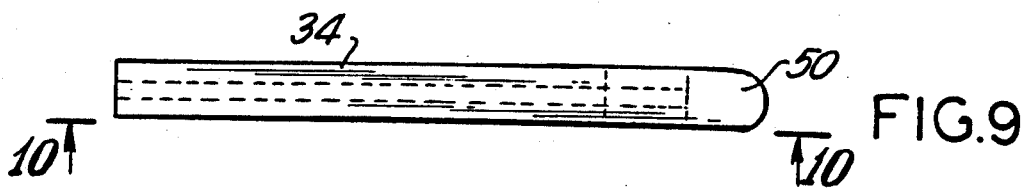
FIG. 9 is a further enlarged plan view of the third type of inventive electrode, this being a digital ring electrode.

Ground electrode 30 is generally circular and has at one circumferential location a protruding arcuate tab 48 for connection to a cable connector (not shown). To potect against delamination during use, a hole 49 is punched where hydrogel layer I and tab 48 meet. Ground electrode 30 is made up of a plurality of laminations that are shown separated in FIG. 8. To proceed inwardly toward the patient's skin from outer face of ground electrode 30, layer G is a label, layer H is conductive foil having a coating of silver/silver chloride, layer I is hydrogel/conductive adhesive and layer J is a backing sheet. More specifically, hole 49 assures contact between adhesive on label G and hydrogel layer I.

Figure 10:
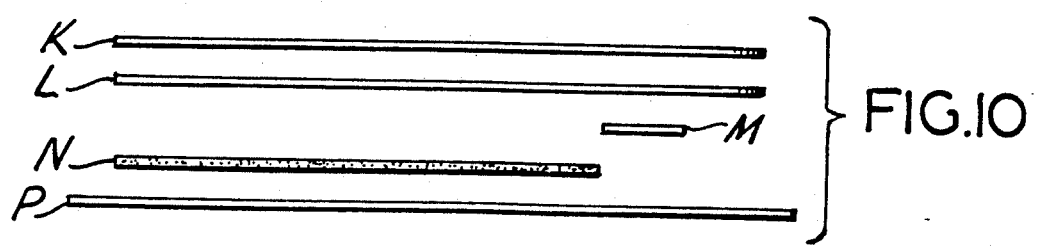
FIG. 10 is a side view of the electrode of FIG. 9 showing the laminations thereof separated, substantially on line 10—10 of FIG. 9.

Digital ring electrode 34, which is flexible and elongated so that it can be wrapped around a patient's digit, such as a finger or a toe, has at one end an arcuate tab 50 for connection to a cable connector (not shown). Digital ring electrode 34 is made up of a plurality of laminations or layers that are shown separated in FIG. 10. To proceed inwardly toward the patient's skin from the outer face of digital ring electrode 34, layer K is a label, layer L is conductive foil having a coating of silver/silver chloride, layer M is sealing foil, layer N is hydrogel/conductive adhesive and layer P is a backing sheet. To protect digital ring electrode 34 against delamination during use, most of the area of hydrogel layer N adhesively engages conductive foil L.

Figure 11:
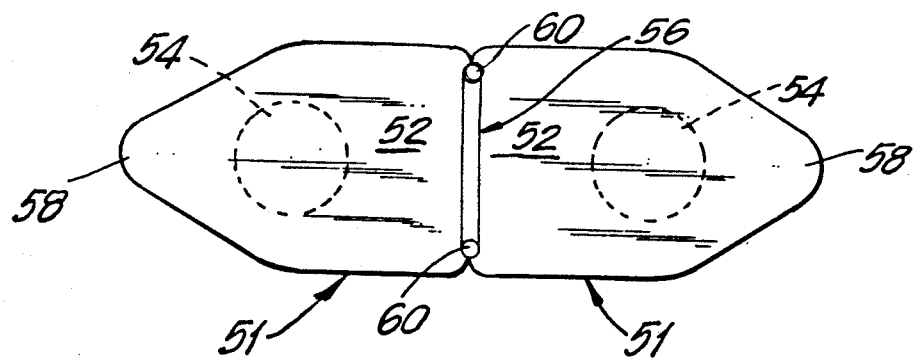
FIG. 11 is a plan view similar to FIG. 5 of a modified preferred disc electrode according to the invention.

FIG. 11 shows a modified disc electrode 51 which, like disc electrode 26, is a double electrode, electrode 51 comprising two electrode elements 52 in one, with two circular conductive gel areas 54, each 10 mm in diameter. The rest of the outer surface is non-conductive. Each electrode element 52 is joined to its neighbor in a central portion 56 that spaces conductive gel areas 54 a precisely controlled constant distance from each other. The end of each electrode element 52 remote from central portion 56 has an arcuate tab 58 for connection to a cable connector (not shown). Between central portion 56 and tab 58 each of the two electrode elements 52 is parallel-sided. Near its opposite ends, central portion 56 has attachment points 60 and may be slightly indented. In central portion 56 between attachment points 60, electrode elements 52 are unconnected. Attachment points 60 add rotation stability to electrode elements 52 when used in the paired mode, at the same time providing easy separability of electrode elements 52 from each other for use in the detached mode.

Two electrodes 51 can be incorporated in kit 20 in place of two electrodes 26 without changing blister pack 22.

Figure 12:
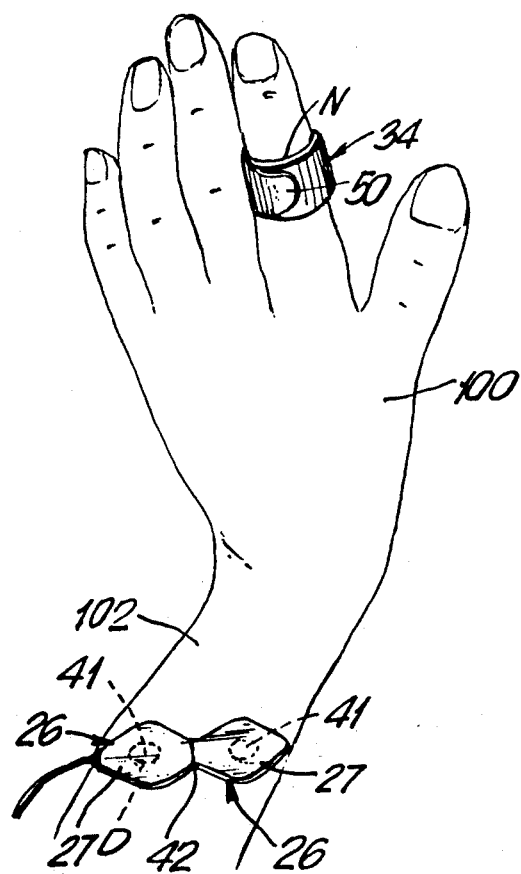
FIG. 12 is a view of a human hand and forearm showing a digital ring electrode applied to the index finger and a double disc electrode applied to the forearm.

FIG. 12 shows a human hand 100 and a connected forearm 102 with digital ring electrode 34 applied to the index finger and double disc electrode 26 applied to forearm 102.

Figure 13:
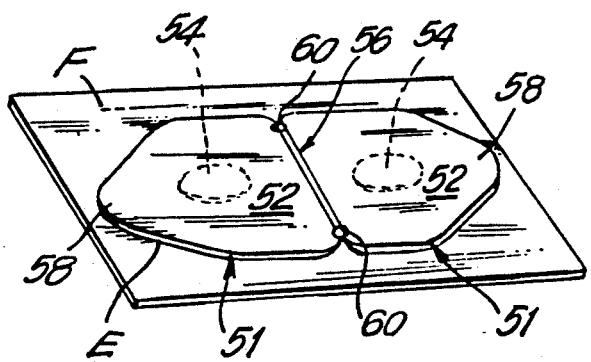
FIG. 13 is a view of the modified disc electrode of FIG. 11 before application thereof to a human being.

FIG. 13 shows double disc electrode 51 prior to use with foam layer E adhered to backing sheet F.

In the case of each of the electrodes disclosed herein, when the backing sheets are removed, the exposed hydrogel/conductive adhesive provides means for adhering the electrode to a patient.

The invention well attains the foregoing objects and advantages, among others. Disclosed details are exemplary only and are not to be taken as limitations on the invention except as these details may be included in the appended claims.

What is claimed is:

1. A disposable disc electrode for use in electromyograph (EMG) and/or nerve conduction velocity (NCV) testing, said electrode comprising first and second identical disc electrode comprising first and second connection to a cable connector and being laminated of a plurality of layers including first and second outer layers, said first outer layer being a backing member with exposable adhesive thereon, a hydrogen layer intermediate said outer layers, and a conductive foil layer between said hydrogel layer and said second outer layer; wherein said eletrode elements are separably joined to each other by a central portion and the tab of each said electrode element is remote from said central portion.

2. The electrode according to claim 1 wherein said second outer layer is a label and said layers further include a foam layer between said backing member and said hydrogel layer and a foam layer between said conductive foil layer and said second outer layer.

3. The electrode according to claim 1 wherein said two disc electrode elements have operative portions that are spaced a precise distance apart.

4. The electrode according to claim 1 wherein each said electrode element has parallel side edges between its said tab and said central portion and said central portion has at opposite lateral ends adjacent each said side edge an attachment point to provide rotation stability and said elements being unconnected between said attachment points to provide easy separability of said electrode elements from each other.

5. The electrode according to claim 4 wherein opposite ends of said central portion are slightly indented.

6. The electrode according to claim 5 wherein said conductive foil layer comprises a silver/silver chloride coating.

7. An electrode according to claim 1 wherein said central portion is of wasp-waist configuration.

8. A packaged assembly of disposable electrodes for use in an electromyography (EMG) and/or nerve conduction velocity (NCV) testing procedure, the assembly comprising in combination at least one disc electrode and at least one ground electrode and at least one digital ring electrode, each of said electrodes of said combination including an element having a tab for connection to a cable connector and being laminated of a plurality of layers including first and second outer layers, said first outer layer being a backing member with exposable adhesive thereon, a hydrogel layer intermediate said outer layers, and a conductive foil layer between said hydrogel layer and said second outer layer, and said disc electrode further comprising two identical disc electrode elements separably jointed to each other by a central portion and the tab of each said disc electrode element being remote from said central portion.

* * * * *

UNITED STATES PATENT AND TRADEMARK OFFICE
CERTIFICATE OF CORRECTION

PATENT NO. : 5,203,330
DATED : April 20, 1993
INVENTOR(S) : Alan J. Schaefer, et al It is certified that error appears in the above-indentified patent and that said Letters Patent is hereby corrected as shown below:

Column 5, line 28 (Claim 1), the word "hydrogen" should read
--hydrogel--.

Signed and Sealed this

Fifteenth Day of February, 1994

Attest:

BRUCE LEHMAN

Attesting Officer          Commissioner of Patents and Trademarks